United States Patent [19]

Cliffe

[11] Patent Number: 4,783,455

[45] Date of Patent: Nov. 8, 1988

[54] SUBSTITUTED PYRIMIDOINDOLES AND DIAZEPINOINDOLES USEFUL AS HYPOGLYCAEMICS

[75] Inventor: Ian A. Cliffe, Cippenham, England

[73] Assignee: John Wyeth and Brother Ltd., Maidenhead, England

[21] Appl. No.: 53,444

[22] Filed: May 22, 1987

[30] Foreign Application Priority Data

Jun. 11, 1986 [GB] United Kingdom ............... 8614246

[51] Int. Cl.⁴ ................ A61K 31/505; A61K 31/55; C07D 487/04

[52] U.S. Cl. .................................. 514/220; 514/267; 540/561; 544/231; 544/252

[58] Field of Search ............... 544/231, 252; 540/561; 514/220, 267

[56] References Cited

U.S. PATENT DOCUMENTS 3,634,426 1/1972 Eberle .................. 540/561
3,850,957 11/1974 White et al. ........... 540/561
3,891,644 6/1975 White .................. 544/252

FOREIGN PATENT DOCUMENTS 1366133 9/1974 United Kingdom.

Primary Examiner—Donald G. Daus
Assistant Examiner—Diana G. Rivers
Attorney, Agent, or Firm—R. K. Jackson

[57] ABSTRACT

Compounds of formula (I)

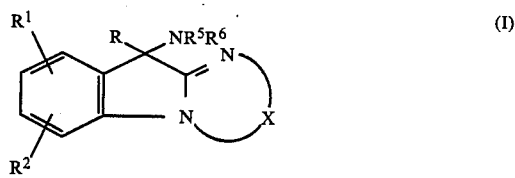

and their pharmaceutically acceptable acid addition salts, wherein R represents lower alkyl or a mono- or bicyclic aryl or heteroaryl radical, $R^1$ and $R^2$ which may be the same or different each represent hydrogen, hydroxyl, lower alkyl, lower alkoxy, halo(lower)alkyl, halogen, amino or mono- or di(lower)alkylamino, X represents —$CH_2CR^3R^4CH_2$— or —$(CH_2)_4$—where $R^3$ and $R^4$ each independently represent hydrogen or lower alkyl or $R^3$ and $R^4$ together with the carbon atom to which they are attached represent a 5, 6 or 7 membered carbocyclic ring and $R^5$ represents acyl and $R^6$ represents hydrogen or $R^5$ and $R^6$ each independently represent hydrogen or lower alkyl, are useful as hypoglycaemics.

16 Claims, No Drawings

SUBSTITUTED PYRIMIDOINDOLES AND DIAZEPINOINDOLES USEFUL AS HYPOGLYCAEMICS

This invention relates to substituted pyrimidoindoles and diazepinoindoles, to processes for their preparation, to their use and to pharmaceutical compositions containing them.

The novel compounds of the present invention are compounds of the general formula (I)

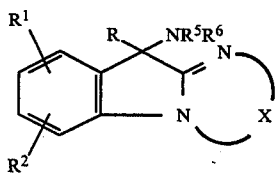

and their pharmaceutically acceptable acid addition salts. In the formula, R represents lower alkyl or a mono- or bicyclic aryl or heteroaryl radical, $R^1$ and $R^2$ which may be the same or different each represent hydrogen, hydroxyl, lower alkyl, lower alkoxy, halo(lower)alkyl, halogen, amino or mono- or di(lower)alkylamino, X represents —$CH_2CR^3R^4CH_2$— or —$(CH_2)_4$— where $R^3$ and $R^4$ each independently represent hydrogen or lower alkyl or $R^3$ and $R^4$ together with the carbon atom to which they are attached represent a 5,6 or 7 membered carbocyclic ring and $R^5$ represents acyl and $R^6$ represents hydrogen or $R^5$ and $R^6$ each independently represent hydrogen or lower alkyl.

The term "lower" as used herein means that the radical referred to contains 1 to 6 carbon atoms. Preferably such radicals contain 1 to 4 carbon atoms. For example, a lower alkyl group may be methyl, ethyl, propyl or butyl and a lower alkoxy may be methoxy, ethoxy, propoxy or butoxy.

The terms "aryl" and "heteroaryl" are used herein to denote radicals having an aromatic character. Such radicals include phenyl, naphthyl and heterocyclic radicals having an aromatic character. For example, R may be a radical such as phenyl, naphthyl, thienyl, pyridyl, indolyl and benzothienyl, each of which may be substituted or unsubstituted. Suitable substituents include those mentioned herein for the definitions of $R^1$ and $R^2$; preferable substituents are halogen (for example fluorine, chlorine or bromine), lower alkyl (for example methyl, ethyl, propyl or butyl), lower alkoxy (for example methoxy, ethoxy, propoxy or butoxy) and halo(lower)alkyl (for example trifluoromethyl). Preferably R is phenyl optionally substituted as mentioned above.

Preferred examples of $R^1$ and $R^2$ residues include hydrogen, lower alkyl (e.g. methyl, ethyl, propyl and butyl), lower alkoxy (e.g. methoxy, ethoxy, propoxy and butoxy, halo(lower)alkyl (e.g. trifluoromethyl) and halogen (e.g. chlorine and bromine).

Preferably Rhu and $R^4$ are both hydrogen or both lower alkyl (e.g. methyl). $R^3$ and $R^4$ together with the carbon atom to which they are attached can also represent a cycloalkyl radical containing 5 to 7 carbon atoms (e.g. cyclohexyl).

$R^5$ and $R^6$ are preferably both hydrogen or one is hydrogen and the other is an acyl group. The acyl group may be derived from a carboxylic acid or other acid such as a sulphonic acid or a sulphonylcarbamic acid. For example the acyl group may be (lower) alkoxycarbonyl, lower alkyl- or aryl-oraryl(lower)alkyl sulphonyl, lower alkyl- or aryl- or aryl(lower)alkylsulphonylcarbamoyl or preferably lower alkylcarbonyl, arylcarbonyl or aryl(lower)alkylcarbonyl where the aryl group is preferably phenyl optionally substituted as mentioned above. A particularly preferred acyl group is (lower)alkylcarbonyl.

The compounds of the invention in which $R^5$ represents a (lower)alkylcarbonyl group and $R^6$ represents hydrogen are amides which may be prepared by reacting a tertiary alcohol of general formula

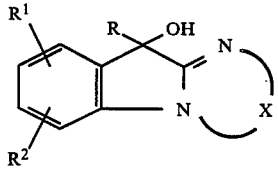

(where X, R, $R^1$ and $R^2$ are as defined above) or an acid addition salt thereof, with an organic nitrile of general formula $$R^7CN \qquad (III)$$

where $R^7$ represents lower alkyl. The tertiary alcohol or the salt thereof may be reacted with the nitrile in the presence of a strong acid (e.g. concentrated sulphuric acid, phosphoric acid or polyphosphoric acid) as in the Ritter reaction (I. I. Krimen and D. J. Cota, Organic Reactions, 1969, 17, 213). The resulting amide may be obtained by dilution of the reaction mixture with water.

The other compounds of the invention may be obtained from the compounds in which $R^5$ represents a (lower)alkylcarbonyl group and $R^6$ represents hydrogen. For example the compound may be hydrolysed (e.g. under acid conditions) to give the primary amine of general formula (I) in which $R^5$ and $R^6$ are both hydrogen. The primary amine may be mono-or di-N-alkylated by methods known in the art to give compounds in which $R^5$ is lower alkyl and $R^6$ is hydrogen or lower alkyl. The amine may also be acylated to give compounds of the invention in which $R^5$ represents acyl and $R^6$ represents hydrogen. The acylating agent may be an acid anhydride (e.g. acetic anhydride), an acyl halide such as an alkanoyl chloride (e.g. acetyl chloride), an aroyl chloride (e.g. benzoyl chloride), a sulphonyl chloride (e.g. methane sulphonyl chloride or toluenesulphonyl chloride) or a sulphonyl isocyanate (e.g. toluenesulphonyl isocyanate).

The tertiary alcohols of the general formula III may be prepared by, for example, reacting a ketone of general formula

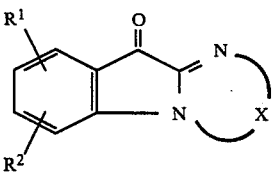

(where $R^1$, $R^2$ and X have the meanings given above) with an organic metallic compound, such as a Grignard reagent, containing the R residue. This process is exemplified in our UK Specification No. 1,366,133.

If in the process described above the compound of the invention is obtained as an acid addition salt, the free base can be obtained by basifying a solution of the acid addition salt. Conversely, if the product of the process is a free base, an acid addition salt, particularly a pharmaceutically acceptable acid addition salt may be obtained by dissolving the free base in a suitable organic solvent and treating the solution with an acid, in accordance with conventional pfocedures for preparing acid addition salts from base compounds.

Examples of acid addition salts are those formed from inorganic and organic acids, such as sulphuric, hydrochloric, hydrobromic, phosphoric, tartaric, fumaric, maleic, citric, acetic, formic, methanesulphonic and p-toluenesulphonic acids.

The compounds of the invention possess at least one asymmetric carbon atom and hence can exist in various stereochemical forms. The stereochemical forms can be separated or isolated by standard procedures. For example resolution of a racemic final product or intermediate may be carried out by known procedures so as to give the product as an optically active enantiomorph.

The compounds of the present invention possess pharmacological activity. For example, the compounds in general possess hypoglycaemic activity and hence are of value in the treatment of diabetes. The compounds of the invention are tested for hypoglycaemic activity by a standard procedure in which the compounds are administered to rats and the blood glucose concentration is determined prior to administration and at various times after dosage. When 10-amino-2,3,4,10-tetrahydro-3,3-dimethyl-10-phenylpyrimido[1,2-a]indole, a representative compound of the invention, was tested by this procedure at 100 mg/kg p.o. the blood glucose concentration was found to be 68% of that of control animals (i.e. rats administered vehicle alone) at 4 hours after administration.

The invention further provides a compound of formula (I) or a pharmaceutically acceptable acid addition salt for use as a hypoglycaemic in a mammal.

The invention also provides a pharmaceutical composition comprising a compound of general formula (I) or a pharmaceutically acceptable acid addition salt thereof in association with a pharmaceutically acceptable carrier. Any suitable carrier known in the art can be used to prepare the pharmaceutical composition. In such a composition, the carrier is generally a solid or liquid or a mixture of a solid and a liquid.

Solid form compositions include powders, granules, tablets, capsules (e.g. hard and soft gelatine capsules), suppositories and pessaries. A solid carrier can be, for example, one or more substances which may also act as flavouring agents, lubricants, solubilisers, suspending agents, fillers, glidants, compression aids, binders or tablet-disintegrating agents; it can also be an encapsulating material. In powders the carrier is a finely divided solid which is in admixture with the finely divided active ingredient. In tablets the active ingredient is mixed with a carrier having the necessary compression properties in suitable proportions and compacted in the shape and size desired. The powders and tablets preferably contain up to 99%, e.g. from 0.03 to 99%, preferably 1 to 80% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

The term "composition" is intended to include the formulation of an active ingredient with encapsulating material as carrier to give a capsule in which the active ingredient (with or without other carriers) is surrounded by the carrier, which is thus in association with it. Similarly cachets are included.

Liquid form compositions include, for example, solutions, suspensions, emulsions, syrups, elixirs and pressurised compositions. The active ingredient, for example, can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavouring agents, suspending agents, thickening agents, colours, viscosity regulators, stabilisers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycerol and glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. When the compound is orally active it can be administered orally either in liquid or solid composition form.

Preferably the pharmaceutical composition is in unit dosage form, e.g. as tablets or capsules. In such form the composition is sub-divided in unit dose containing appropriate quantities of the active ingredient; The unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form. The quantity of the active ingredient in unit dose of composition may be varied or adjusted from 0.5 mg or less to 750 mg or more, according to the particular need and the activity of the active ingredient. The invention also includes the compounds in the absence of the carrier where the compounds are in unit dosage form.

The following Examples illustrate the invention:

EXAMPLE 1

10-Acetamido-10-(3-chlorophenyl)-2,3,4,10-tetrahydropyrimido[1,2-a]indole

Concentrated sulphuric acid (12 ml) was added dropwise over 5 minutes to vigorously stirred acetonitrile (24 ml) at 0°–5°. The resulting colourless solution was treated in one portion with 10-(3-chlorophenyl)-2,3,4,10-tetrahydropyrimido[1,2-a]indol -10-ol (3.0 g). The mixture was immediately stirred and heated at 50°–60° whereupon solution occurred within 5 minutes. After 1 hour, the solution was poured onto ice (100 ml) and the mixture was basified with saturated aqueous ammonia (90 ml) and extracted with dichloromethane (3×60 ml). The extracts were dried (MgSO$_4$) and evaporated in vacuo. The residue was triturated with ethyl acetate to give light brown crystals which were purified by flash chromatography (Al$_2$O$_3$, ethyl acetate), trituration with ethanol-ether (1:1), and washing with ether to give the title compound free base as a colourless powder.

The free base was dissolved in dichloromethane-methanol (4:1) and acidified with ethereal HCl to give the title compound as the hydrochloride (0.19 g), m.p. 275°–285° (dec.).

Found: C, 59.7; H, 5.1; N, 11.0% . C$_{19}$H$_{18}$ClN$_3$O.HCl.¼H$_2$O requires C, 59.9; H, 5.1; N, 11.0%.

EXAMPLE 2

10-Amino-10-(3-chlorophenyl)-2,3,4,10-tetrahydropyrimido[1,2-a]indole

A solution of the product of Example 1 (2.48 g) in hydrochloric acid 36% w/w (10 ml) was heated at 120° with stirring for 2½ hours, cooled to room temperature, diluted with H$_2$O (50 ml), washed with ethyl acetate (3×50 ml), basified with 33% aqueous ammonia and extracted with chloroform (3×100 ml). The extracts were washed with brine (100 ml), dried (MgSO$_4$) and evaporated in vacuo. The oil was dissolved in methanol (10 ml), acidified with ethereal HCl, and evaporated in vacuo to give a solid which was triturated with ether (3×10 ml) to give the title compound as the hydrochloride (1.83 g) as colourless crystals, m.p. 274°–276° (dec.).

Found: C, 55.1; H, 4.8; N, 10.95% . C$_{17}$H$_{16}$ClN$_3$.2HCl requires C, 55.1; H, 4.9; N, 11.3%.

EXAMPLE 3

10-Acetamido-2,3,4,10-tetrahydro-10-phenylpyrimido[1,2-a]indole

A solution of 2,3,4,10-tetrahydro-10-phenylpyrimido[1,2-a]indol-10-ol (7.15 g) in acetonitrile (50 ml) and methanesulphonic acid (3 ml) was added dropwise with caution over 25 minutes to a pre-heated flask containing stirred sulphuric acid 98% w/w (28 ml) at such a rate that the temperature remained steady at 51°–56°. The solution was cooled to room temperature, poured into water (200 ml) and basified with sodium hydroxide (40 g) and sodium carbonate. The mixture was extracted with chloroform (3×200 ml) and the extracts washed with brine (50 ml), dried (MgSO$_4$), and evaporated in vacuo. The yellow solid was triturated with ethyl acetate to give a first crop of the product free base (2.735 g) as a colourless powder. The triturates were purified by chromatography (Al$_2$O$_3$; ethyl acetate) to give a second crop of the product free base (1.16 g) also as a colourless powder.

The first crop of the product free base was suspended in methanol (8 ml), acidified with ethereal HCl, and the resulting solution evaporated in vacuo to give an oil which on trituration with ethyl acetate and ether gave the title compound as the hydrochloride (3.01 g), m.p. 315°–325° (dec.).

Found: C, 66.3; H, 6.1; N, 12.5%. C$_{19}$H$_{19}$N$_3$O.HCl requires C, 66.75; H, 5.9; N, 12.3%.

EXAMPLE 4

10-Amino-10-phenyl-2,3,4,10-tetrahydropyrimido[1,2-a]indole

A solution of the product of Example 3 (1.01 g) in hydrochloric acid 36% w/w (15 ml) was heated with stirring at 110° for 5 hours. The mixture of liquid and precipitate was cooled to room temperature, dissolved in water (40 ml), washed with ethyl acetate (2×100 ml), basified with 33% aqueous ammonia, extracted with dichloromethane (2×100 ml) and the extracts washed with brine (50 ml), dried (MgSO$_4$), and evaporated in vacuo to give the title compound as a free base. The solid was suspended in methanol (5 ml), acidified with ethereal hydrochloric acid, and the resulting solution evaporated in vacuo to give the crude product as a dihydrochloride. The product was recrystallised from methanol - ethyl acetate to give two crops of product: Crop A as colourless crystals (0.49 g), m.p. 260°–265° (dec.)

Found: C, 60.7; H, 6.0; N, 12.2% . C$_{17}$H$_{17}$N$_3$.2HCl requires C, 60.7; H, 5.7; N, 12.5% and Crop B as colourless crystals (0.22 g), m.p. 260°–265° (dec.)

Found: C, 60.2; H, 6.1; N, 11.9% . Calculated for C$_{17}$H$_{17}$N$_3$.2HCl.¼H$_2$O: C, 59.9; H, 5.8; N, 12.3%.

EXAMPLE 5

10-Acetamido-2,3,4,10-tetrahydro-3,3-dimethyl-10phenylpyrimido[1,2-a]indole

A solution of 2,3,4,10-tetrahydro-10-phenylpyrimido [1,2-a]indol-10-ol (10.38 g) in acetonitrile (75 ml) and methanesulphonic acid (4.2 ml)was added dropwise with judicious cooling over 40 min to a pre-heated flask containing stirred sulphuric acid 98% w/w (38 ml) at such a rate that the temperature remained steady at 50°–55°. The solution was cooled to room temperature, poured into water (600 ml), and basified with sodium hydroxide (50 g,1.25 mol) and sodium carbonate. The mixture was extracted with chloroform (3×350 ml) and the combined extracts were washed with water (350 ml), dried (MgSO$_4$), and evaporated in vacuo to give the title compound as a colourless solid (10.03 g).

The sample was converted into the hydrochloride salt, m.p. >300°.

Found: C, 66.9; H, 6.65; N, 11.2. C$_{21}$H$_{23}$N$_3$O.HCl.½H$_2$O requires C, 66.6; H, 6.65; N, 11.1% .

EXAMPLE 6

10-Amino-2,3,4,10-tetrahydro-3,3-dimethyl-10-phenylpyrimido[1,2-a]indole

A solution of the product free base from Example 5 (7.76 1 g) in hydrochloric acid 36% w/w (35ml) was heated with stirring at 110° for 3.5 h, cooled to room temperature, dissolved in water (350 ml), basified with 33% aqueous ammonia, extracted with chloroform (2×200 ml) and the extracts washed with water (350 ml), dried (MgSO$_4$), and evaporated in vacuo to give the title compound as a free base (4.13 g). A sample of the free base was converted into the dihydrochloride salt, m.p. 260°–265° (dec).

Found: C, 62.0; H, 6.3; N, 11.2. C$_{19}$H$_{21}$N$_3$.2HCl.¼H$_2$O requires C, 61.9; H, 6.4; N, 11.4%.

EXAMPLE 7

10-Acetamido-2,3,4,10-tetrahydro-10-methylpyrimido[1,2-a]indole

A solution of 2,3,4,10-tetrahydro-10-methylpyrimido [1,2-a]indol-10-ol (0.444 g) in acetonitrile (4 ml) and methanesulphonic acid (10 drops) was adde dropwise over 5 min to stirred sulphuric acid 98% w/w (2.5 ml) at 50°–60°. After 2.5h, the solution was poured into water (100 ml), basified with sat. aqueous sodium bicarbonate, and extracted with chloroform (3×100 ml).

The extracts were washed with water (200 ml), dried (MgSO$_4$), and evaporated in vacuo to give the title compound as the free base (0.07 g).

The hydrochloride of the title compound was prepared from methanol-ether as hygroscopic brown crystals, m.p. 255°–260° (dec.).

Found: C, 57.7; H, 6.8; N, 14.2. C$_{14}$H$_{17}$N$_3$O.HCl.¼H$_2$O requires C, 57.3; H, 6.7; N, 14.3%.

EXAMPLE 8

2,3,4,10-Tetrahydro-3,3-dimethyl-10-methylsulphonylamino-10-phenylpyrimido[1,2-a]indole Methanesulphonyl chloride (1 ml) was added to the product free base from Example 6 (1.20 g) in dry pyridine (50 ml). After 1 hour the solution was evaporated in vacuo and the residual oil dissolved in dichloromethane (50 ml), washed with water (50 ml), saturated aqueous sodium bicarbonate (50 ml), and water (50 ml), dried (MgSO$_4$), evaporated in vacuo, and purified by chromatography (Al$_2$O$_3$; ethyl acetate to give the free base of the title product as a brown solid (0.39 g).

The hydrochloride salt, m.p. 160°–165° (dec) was prepared from ether-methanol.

Found: C, 57.0; H, 6.0; N, 9.9. C$_{20}$H$_{23}$N$_3$O$_2$S.HCl.¾H$_2$O requires C, 57.3; H, 6.1; N, 10.0%.

EXAMPLE 9

10'-Acetamido-2',3',4',10'-tetrahydro-10'-phenylspiro[cyclohexane-1,3'-pyrimido[1,2-a]indole]

A solution of 10'-hydroxy-10'-phenyl-2',3',4',10'-tetrahydrospiro[cyclohexane-1,3'-pyrimido[1,2-a]indole]-hydrochloride (1.073 g), in acetonitrile (10 ml) and methanesulphonic acid (90 drops) was added dropwise over 20 min to sulphuric acid 98% w/w (4 ml) at 45°–55° with stirring. After 1 hour, the solution was poured into water (100 ml) and the mixture was basified with 1N-sodium hydroxide and extracted with chloroform (3×100 ml). The extracts were washed with water (100 ml), dried (MgSO$_4$), and evaporated in vacuo to give a solid. The solid was dissolved in methanol and the solution acidified with ethereal HCl and evaporated in vacuo to give the title compound as the hydrochloride (0.06 g), m.p. >300°.

Found: C, 67.65; H, 7.0; N, 9.5. C$_{24}$H$_{27}$N$_3$O.HCl.H$_2$O requires C, 67.4; H, 7.1; N, 9.8%.

EXAMPLE 10

11-Acetamido-2,3,4,5-tetrahydro-11-phenyl-11H-[1,3]diazepino[1,2-a]indole

A suspension of 2,4,5,11-tetrahydro-11-phenyl-3H-[1,3]diazepino[1,2-a]indol-11-ol hydrobromide (2.89 g) in acetonitrile (16 ml) and methanesulphonic acid (100 drops) was added dropwise over 10 min to stirred sulphuric acid 98% w/w (8 ml) at 50°–60°. After ½ hour, the solution was cooled to room temperature, poured into water (200 ml), basified with sodium hyroxide (10 g) and sodium carbonate and extracted with chloroform (2×200 ml). The extracts were dried (MgSO$_4$) and evaporated in vacuo. The brown oil was purified by chromatography (Al$_2$O$_3$; ethyl acetate) to give the product free base (0.82 g) as a colourless solid. The hydrochloride was prepared from ether-methanol as a solid (1.06 g), m.p. 285°–290° (dec.).

Found: C, 64.5; H, 6.2; N, 11.3. C$_{20}$H$_{21}$N$_3$O.HCl.H$_2$O requires C, 64.25; H, 6.5; N, 11.2%.

EXAMPLE 11

10-Acetamido-2,3,4,10-tetrahydro-10-(2-naphthyl)-pyrimido [1,2-a]indole 10-(2-Naphthyl)-2,3,4,10-tetrahydropyrimdo [1,2-a]indol-10-ol hydrochloride (1.89 g) in acetonitrile (12 ml) and methanesulphonic acid (120 drops) was added dropwise over 15 min to sulphuric acid 98 w/w (6 ml) with stirring at 54°–64°. After ½ hour, the solution was cooled to room temperature, poured into water (200 ml), and basified with sodium hydroxide (7.5 g) and sodium carbonate. The precipitate was filtered, washed with water (2×50 ml), and air-dried to give a brown solid (0.65 g). The filtrate was extracted with chloroform (2×200 ml) and the extracts dried (MgSO$_4$) and evaporated in vacuo to give an oil (0.47 g). The solid and the oil were combined and purified by chromatography (Al$_2$O$_3$; ethyl acetate) to give the product free base (0.34 g) as a foam. The foam was dissolved in methanol (1 ml) and the solution acidified with ethereal HCl (5 ml) and evaporated in vacuo to give a foam which was induced to crystallise by trituration with ethyl acetate to give the title compound as the hydrochloride (0.31 g), m.p. 265–268 (dec).

Found: C, 69.9; H, 5.75; N, 10.9. C$_{23}$H$_{21}$N$_3$O.HCl.¼H$_2$O requires C, 69.7; H, 5.7; N, 10.6%.

EXAMPLE 12

10'-Acetamido-2',3',4',10'-tetrahydro-10'-phenylspiro [cyclopentane-1,3'-pyrimido[1,2-a]indol]

2',3',4',10'-Tetrahydro-10'-hydroxy-10'-phenylspiro [cyclopentane-1,3'-pyrimido[1,2-a]indole](2 g) in acetonitrile (16 ml) and methanesulphonic acid (100 drops) was added dropwise over 10 min to sulphuric acid 98% w/w (8 ml) at 50°–60° with stirring. After ½ hour the solution was cooled to room temperature, poured into water (200 ml), and basified with 1M-sodium hydroxide. The mixture was extracted with chloroform (2×200 ml) and the extracts dried (MgSO$_4$) and evaporated in vacuo to give a solid which was purified by chromatography [Al$_2$O$_3$; chloroform-methanol (100:1)]. The yellow solid was dissolved in methanol (2 ml), acidified with ethereal HCl (5 ml), and evaporated in vacuo to give a glass. Trituration with ethyl acetate gave the title compound as the hydrochloride (0.5 g), m.p. >300°.

Found: C, 69.2; H, 6.8; N, 10.2. C$_{23}$H$_{25}$N$_3$O.HCl.¼H$_2$O requires 69.0; H, 6.7; N, 10.5%.

EXAMPLE 13

10-Butanamido-2,3,4,10-tetrahydro-3,3-dimethyl-10-phenylpyrimido[1,2-a]indole 2,3,4,10-Tetrahydro-10-phenylpyrimido[1,2-a]indol-10-ol (2.19 g) in butyronitrile (16 ml) and methanesulphonic acid (100 drops) was added dropwise over 10 min to sulphuric acid 98% w/w (8 ml) at 50°–60° with stirring. After ½ hour, the solution was poured into water (200 ml), basified with 1N-sodium hydroxide, and extracted with chloroform (2×200 ml). The extracts were washed with 1M-sodium hydroxide (100 ml) and water (100 ml), dried (MgSO$_4$), and evaporated in vacuo to give the product free base as a solid (0.67 g). The solid was dissolved in methanol (2 ml, acidified with ethereal-HCl (5 ml), and evaporated in vacuo to give the title compound as the hydrochloride (0.6 g), m.p. 275°–280° (dec).

Found: C, 68.9; H, 7.3; N, 10.2. $C_{23}H_{27}N_3O \cdot HCl \cdot \frac{1}{4}H_2O$ requires C, 68.7; H, 7.1; N, 10.4%.

EXAMPLE 14

2,3,4,10-Tetrahydro-3,3-dimethyl-10-[3-(4-methylphenylsulphonyl)ureido]10-phenylpyrimido[1,2-a]indole 4-Toluenesulphonyl isocyanate (1.0 g) in acetonitrile(5 ml) was added dropwise to a stirred solution of the product free base from Example 6 (1.17 g) in acetonitrile (50 ml). After 1 hour, the solution was evaporated in vacuo to give a glass which was induced to crystallise by trituration with ethyl acetate-methanol (5:1, 6 ml). The solid was suspended in methanol (30 ml) and ethereal-HCl (4 ml) added. A solution was formed from which a solid precipitated after a few minutes. The solid was filtered, washed with ether, and dried in vacuo to give the title compound as the hydrochloride (1.69 g), m.p. 253°–255° (dec.)

Found: C, 61.5; H, 5.7; N, 10.5. $C_{27}H_{28}N_4SO_3 \cdot HCl$ requires C, 61.8; H, 5.6; N, 10.7%.

EXAMPLE 15

10-Benzamido-2,3,4,10-tetrahydro-3,3-dimethyl-10-phenylpyrimido[1,2-a]indole

Benzoyl chloride (0.9 ml) was added dropwise to the product free base from Example 6 (1.12 g) in triethylamine (1 ml) pyridine (40 ml). After 1 hour, the solution was evaporated in vacuo. The residue was azeotroped in vacuo with toluene (50 ml) and dissolved in dichloromethane (50 ml). The solution was washed with water (2×100 ml), dried (MgSO$_4$), and evaporated in vacuo to give a yellow foam which crystallised from ether-dichloromethane (1:). The solid was recrystallised from ethyl acetate-cyclohexane to give a first crop of the product (0.59 g), m.p. 183°–185°. The filtrate was purified by chromatography (Al$_2$O$_3$; ether) and trituration with ether to give a second crystalline crop of the product (0.70 g). The two crops of the free base were combined, suspended in methanol (5 ml), and acidified with ethereal HCl. The solution was evaporated in vacuo to give a glass which crystallised from boiling ethyl acetate as the title compound hydrochloride (0.99 g), m.p. 295°–298° (dec.)

Found: C, 72.4; H, 6.1; N, 9.4. $C_{26}H_{25}N_3O \cdot HCl$ requires C, 72.3; H, 6.1; N, 9.7%.

EXAMPLE 16

2,3,4,10-Tetrahydro-3,3-dimethyl-10-(4-methylphenylsulphonamido)-10-phenylpyrimido[1,2-a]indole Toluene-4-sulphonyl chloride (1.3 g) was added to the product free base from Example 6 (1.03 g) in pyridine (40 ml) and triethylamine (1 ml) with stirring and, after 1.5 hour, the solution was evaporated in vacuo. The residue was dissolved in dichloromethane (50 ml) and the solution washed with water (2×100 ml), dried (MgSO$_4$), and evaporated in vacuo to give a red foam (1.82 g).

The foam crystallised from ethyl acetate as a yellow solid (0.52 g) which was purified by recrystallisation from propan-2-ol/di-iso-propyl ether to give the title compound (0.27 g), m.p. 224°–226°.

Found: C, 69.5; H, 6.25; N,, 9.2. $C_{26}H_{27}N_3O_2S \cdot \frac{1}{4}H_2O$ requires: C, 69.4; H, 6.2; N, 9.3%.

The ethyl acetate filtrate was purified by chromatography (Al$_2$O$_3$; ethyl acetate) to give a second crop of title (0.28 g).

EXAMPLE 17

2,3,4,10-Tetrahydro-10-ethoxycarbonylamino-3,3-dimethyl-10-phenylpyrimido[1,2-a]indole Ethyl chloroformate (0.9 ml) was added to the product free base from Example 6 (1.32 g) in pyridine (40 ml) and triethylamine (1 ml) with stirring and, after 2 hours, the solution was evaporated in vacuo. The residue was dissolved in dichloromethane (50 ml) and the solution washed with water (2×100 ml), dried (MgSO$_4$), and evaporated in vacuo to give a red oil (1.59 g). The residue was purified by chromatography to give a yellow oil (0.62 g) which slowly crystallised on trituration with ether as the title compound (0.29 g), m.p. 169°–171°.

Found: C, 72.4; H, 6.8; N, 11.4. $C_{22}H_{25}N_3O_2$ requires: C, 72.7; H, 6.9; N, 11.6%.

EXAMPLE 18

10-Acetamido-2,3,4,10-tetrahydro-3,3-dimethyl-10-phenylpyrimido[1,2-a]indole

Method A

The product free base from Example 6 (0.093 g) was dissolved in acetic anhydride (10 ml) and after 4½ hours the solution was evaporated in vacuo. The residue was dissolved in dichloromethane (50 ml) and the solution washed with saturated aqueous sodium bicarbonate (50 ml) and water (50 ml), dried (MgSO$_4$), and evaporated in vacuo to give the title compound free base (0.106 g), m.p. 233°–235°.

Method B

A solution of the product free base from Example 6 (0.137 g) and triethylamine (0.1 ml) in pyridine (5 ml) was treated dropwise with acetyl chloride (0.1 ml) and after 2 hours evaporated in vacuo. The residue was partioned between water (50 ml) and dichloromethane (70 ml) and the organic phase washed with brine (50 ml), dried (MgSO$_4$), and evaporated in vacuo. The residue was azeotroped in vacuo with toluene to give the title compound free base (0.03 g) as a light yellow solid, m.p. 230°–232°.

I claim:

1. A compound of the formula:

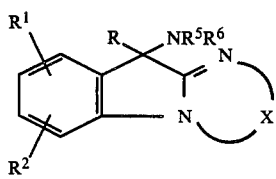

in which

R is alkyl of 1 to 6 carbon atoms or substituted or unsubstituted phenyl, in which the substituents are hydroxyl, alkyl of 1 to 6 carbon atoms, alkoxy of 1 to 6 carbon atoms, haloalkyl of 1 to 6 carbon atoms, halo, amino, alkylamino of 1 to 6 carbon atoms or dialkylamino of 2 to 12 carbon atoms;

$R^1$ and $R^2$ are, independently, hydrogen, hydroxyl, alkyl of 1 to 6 carbon atoms, alkoxy of 1 to 6 carbon atoms, haloalkyl of 1 to 6 carbon atoms, halo, amino, alkylamino of 1 to 6 carbon atoms or dialkylamino of 2 to 12 carbon atoms;

X is —CH$_2$—CR$^3$R$^4$—CH$_2$— or —(CH$_2$)$_4$— where R$^3$ and R$^4$, independently, are hydrogen or alkyl of 1 to 6 carbon atoms, and, when taken together with the carbon atom to which they are attached, R$^3$ and R$^4$ complete a cyclopentane, cyclohexane or cycloheptane ring;

R$^5$ and R$^6$, independently, are hydrogen or alkyl of 1 to 6 carbon atoms, or R$^6$ is hydrogen and R$^5$ is alkylcarbonyl, where the alkyl group is of 1 to 6 carbon atoms;

or a pharmaceutically acceptable salt thereof.

2. A compound of claim 1 in which R is phenyl or phenyl substituted by one or more halogen, alkyl of 1 to 4 carbon atoms, alkoxy of 1 to 4 atoms or haloalkyl substituent of 1 to 4 carbon atoms.

3. A compound of claim 1 in which X is —CH$_2$CR$^3$R$^4$CH$_2$— wherein R$^3$ and R$^4$ are hydrogen or alkyl of 1 to 4 carbon atoms or when taken together with the carbon atom to which they are attached, they complete a cyclopentane, cyclohexane or cycloheptane ring.

4. A compound of claim 1 in which R$^5$ is alkanoyl of 2 to 7 carbon atoms and R$^6$ is hydrogen.

5. A compound according to claim 1 which is 10-Amino-2,3,4,10-tetrahydro-3,3-dimethyl-10-phenyl-pyrimido[1,2-a]indole or a pharmaceutically acceptable acid addition salt thereof.

6. A compound of claim 1 which is 10-acetamido-10-(3-chlorophenyl)-2,3,4,10-tetrahydropyrimido[1,2-a]indole, or a pharmaceutically acceptable salt thereof.

7. A compound of claim 1 which is 10-amino-10-(3-chlorophenyl)-2,3,4,10-tetrahydropyrimido[1,2-a]indole, or a pharmaceutically acceptable salt thereof.

8. A compound of claim 1 which is 10-acetamido-2,3,4,10-tetrahydro-10-phenylpyrimido[1,2-a]indole, or a pharmaceutically acceptable salt thereof.

9. A compound of claim 1 which is 10-amino-10-phenyl-2,3,4,10-tetrahydropyrimido[1,2-a]indole, or a pharmaceutically acceptable salt thereof.

10. A compound of claim 1 which is 10-acetamido-2,3,4,10-tetrahydro-3,3-dimethyl-10-phenyl-pyrimido[1,2-]indole, or a pharmaceutically acceptable salt thereof.

11. A compound of claim 1 which is 10-acetamido-2,3,4,10-tetrahydro-10-methylpyrimido[1,2-a]indole, or a pharmaceutically acceptable salt thereof.

12. A compound of claim 1 which is 10'-acetamido-2',3',4',10'-tetrahydro-10'-phenylspiro[cyclohexane-1,3'-pyrimido[1,2a]indole], or a pharmaceutically acceptable salt thereof.

13. A compound of claim 1 which is 11-acetamido-2,3,4,5-tetrahydro-11-phenyl-11H-[1,3]diazepino[1,2-a]indole, or a pharmaceutically acceptable salt thereof.

14. A compound of claim 1 which is 10'-acetamido-2',3',4',10'-tetrahydro-10'-phenylspiro[cyclopentane-1,3'-pyrimido[1,2-a]indole], or a pharmaceutically acceptable salt thereof.

15. A compound of claim 1 which is 10-butanamido-2,3,4,10-tetrahydro-3,3-dimethyl-10-phenyl-pyrimido[1,2-a]indole, or a pharmaceutically acceptable salt thereof.

16. A method of treating diabetes which comprises administering to a mammal in need thereof, a hypoglycemically effective amount of a compound of the formula:

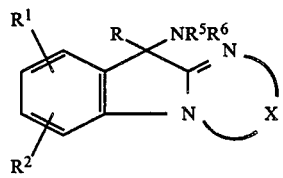

in which

R is alkyl of 1 to 6 carbon atoms, or substituted or unsubstituted phenyl, in which the substituents are hydroxyl, alkyl of 1 to 6 carbon atoms, alkoxy of 1 to 6 carbon atoms, haloalkyl of 1 to 6 carbon atoms, halo, amino, alkylamino of 1 to 6 carbon atoms or dialkylamino of 2 to 12 carbon atoms;

R$^1$ and R$^2$ are, independently, hydrogen, hydroxyl, alkyl of 1 to 6 carbon atoms, alkoxy of 1 to 6 carbon atoms, haloalkyl of 1 to 6 carbon atoms, halo, amino, alkylamino of 1 to 6 carbon atoms or dialkylamino of 2 to 12 carbon atoms;

X is —CH$_2$ —CR$^3$R$^4$—CH$_2$— or —(CH$_2$)$_4$— where R$^3$ and R$^4$, independently, are hydrogen or alkyl of 1 to 6 carbon atoms, and, when taken together with the carbon atom to which they are attached, R$^3$ and R$^4$ complete a cyclopentane, cyclohexane or cycloheptane ring;

R$^5$ and R$^6$, independently, are hydrogen or alkyl of 1 to 6 carbon atoms, or R$^6$ is hydrogen and R$^5$ is alkylcarbonyl, where the alkyl group is of 1 to 6 carbon atoms;

or a pharmaceutically acceptable salt thereof.

* * * * *